(12) United States Patent
Kasuga et al.

(10) Patent No.: US 6,624,126 B1
(45) Date of Patent: Sep. 23, 2003

(54) PERSONAL CLEANSING COMPOSITION COMPRISING A GLYCERYL ETHER

(75) Inventors: Kennichi Kasuga, Tokyo (JP); Tetsuya Miyajima, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/129,273

(22) PCT Filed: Oct. 27, 2000

(86) PCT No.: PCT/JP00/07591
§ 371 (c)(1),
(2), (4) Date: Aug. 8, 2002

(87) PCT Pub. No.: WO01/32134
PCT Pub. Date: May 10, 2001

(30) Foreign Application Priority Data

Nov. 4, 1999 (JP) ............................................. 11-313560

(51) Int. Cl.[7] .............................. C11D 1/83; C11D 3/48
(52) U.S. Cl. ..................... 510/131; 510/130; 510/138; 510/155; 510/156; 510/235; 510/237; 510/356; 510/382; 510/384; 510/388
(58) Field of Search ................................ 510/130, 131, 510/138, 155, 156, 235, 237, 356, 382, 384, 388

(56) References Cited

U.S. PATENT DOCUMENTS

| | | | | |
|---|---|---|---|---|
| 4,985,547 A | * | 1/1991 | Yano et al. ................... 536/4.1 |
| 5,236,612 A | * | 8/1993 | Rahman et al. ............. 252/89.1 |
| 5,863,945 A | * | 1/1999 | Murayama et al. ......... 514/563 |
| 6,437,002 B1 | * | 8/2002 | Ito et al. ...................... 514/724 |

FOREIGN PATENT DOCUMENTS

| | | |
|---|---|---|
| DE | 43 39 368 A | 5/1995 |
| EP | 843002 | 5/1998 |
| EP | 1 013 754 A | 6/2000 |
| EP | 1 092 761 A2 | 4/2001 |
| GB | 1111708 | 5/1968 |
| JP | 57-119998 | 7/1982 |
| JP | 07-003289 | 1/1995 |
| JP | 10-147795 | 6/1998 |
| JP | 10-183173 | 7/1998 |
| JP | 10-245590 | 9/1998 |
| JP | 11-189796 | 7/1999 |
| JP | 11-256198 | * 9/1999 |
| WO | WO 93/09214 | 5/1993 |
| WO | WO 97/46214 A | 12/1997 |
| WO | WO 98/23258 | 6/1998 |

OTHER PUBLICATIONS

Derwent Publications Ltd. , Abstract , 1p., Detergent Composition Kitchen Tableware Containing Alpha Mono Methyl Branch Alkyl Glyceryl Ether Anion Nonionic Amphoteric Surfactant Mixture & JP 57 133200A (Kao Soap Co.), Aug. 17, 1982.

Patent Abstracts of Japan, & JP 11 189790 A (Kao Corp.), Jul. 13, 1999 , Liquid Detergent Composition.

Patent Abstracts of Japan, vol. 1999, No. 12, Oct. 29, 1999 & JP 11 193396 A (Lion Corp), Jul. 21, 1999, Anionic Surfactant and Detergent Composition Containing Same.

* cited by examiner

*Primary Examiner*—Charles Boyer
(74) *Attorney, Agent, or Firm*—Oblon, Spivak, McClelland, Maier & Neustadt, P.C.

(57) ABSTRACT

Detergent compositions containing (A) an anionic surfactant, (B) an antibacterial agent, and (C) a glyceryl ether having a $C_{4-12}$ alkyl or alkenyl group. The compositions are excellent in detergency and quick foaming properties, have high antibacterial action and bring about sufficient antipruritic and deodorant effects on the scalp or body and antidandruff effects on the scalp.

17 Claims, No Drawings

PERSONAL CLEANSING COMPOSITION COMPRISING A GLYCERYL ETHER

TECHNICAL FIELD

The present invention relates to detergent compositions excellent in detergency and quick foaming properties, exhibiting a high antibacterial activity, and producing satisfactory antipruritic and deodorant effects on the scalp or the body and anti-dandruff effects on the scalp.

BACKGROUND ART

Hair or body detergent compositions tend to contain an anionic surfactant as a main base in order to impart them with excellent detergency, foaming power and quick foaming properties. Such detergent compositions are required to have, in addition to cleansing effects, bactericidal or antibacterial effects. Detergent compositions containing an antibacterial agent, such as triclosan, piroctone olamine or a cationic surfactant are known as those for preventing dandruff or itching.

Use of an anionic surfactant and an antibacterial agent in combination however causes such problems as deterioration in detergency or quick foaming properties and insufficient exhibition of antibacterial effects.

An object of the present invention is to provide detergent compositions excellent in detergency and quick foaming properties and bringing about high antibacterial effects.

DISCLOSURE OF THE INVENTION

The present inventors have found that detergent compositions excellent in detergency and quick foaming properties, bringing about high antibacterial effects and exhibiting sufficient antipruritic, deodorant and antidandruff effects are available by using a specific glyceryl ether in combination with an anionic surfactant and an antibacterial agent.

The present invention provides a detergent composition comprising the following components (A), (B) and (C):

(A) an anionic surfactant, (B) an antibacterial agent, and (C) a glyceryl ether having a $C_{4-12}$ alkyl or alkenyl group.

BEST MODE FOR CARRYING OUT THE INVENTION

The anionic surfactants serving as Component (A) in the present invention are preferably those of sulfate, sulfonate and carboxylate types. Examples include alkyl sulfates, polyoxyalkylene alkyl ether sulfates, polyoxyalkylene alkenyl ether sulfates, alkyl sulfosuccinates, polyoxyalkylene alkyl sulfosuccinates, alkylbenzene sulfonates, α-olefin sulfonates, polyoxyalkylene alkylphenyl ether sulfates, glyceride sulfates, amide ether sulfates, higher fatty acid salts, alkane sulfonates and α-sulfo fatty acid ester salts.

Of these anionic surfactants, alkyl sulfates, polyoxyalkylene alkyl ether sulfates and polyoxyalkylene alkenyl ether sulfates are preferred, with alkyl sulfates represented by the below-described formula (5), and polyoxyalkylene alkyl ether sulfates and polyoxyalkylene alkenyl ether sulfates represented by the below-described formula (6) being more preferred.

$$R^7OSO_3M \quad (5)$$

$$R^8O(CH_2CH_2O)_mSO_3M \quad (6)$$

wherein, $R^7$ represents a $C_{10-18}$ alkyl group, $R^8$ represents a $C_{10-18}$ alkyl or alkenyl group, M represents an alkali metal, alkaline earth metal, ammonium, an alkanolamine or a basic amino acid, and m stands for 1 to 5 on the weight average.

As Component (A), at least one anionic surfactant can be used. In order to impart the detergent composition with excellent detergency and foaming performance, it is preferably incorporated in an amount of 5 to 50 wt. %, especially 8 to 30 wt. %, more preferably 10 to 22 wt. % in the whole composition.

Examples of the antibacterial agent as Component (B) to be used in the invention include triclosan, triclocarban, piroctone olamine, zinc pyrithione, selenium disulfide and 3-methyl-4-(1-methylethyl)phenol, and antibacterial agents as described in "Science of Antiseptics·Bactericides of Cosmetics and Pharmaceuticals" (ed. by John. J. Kavala, published by Fragrance Journal), of which triclosan, triclocarban, piroctone olamine and zinc pyrithione are especially preferred.

Examples of the cationic surfactants as Component (B) include quaternary ammonium salts represented by the below-described formula (1), benzalkonium salts or benzethonium salts represented by the formula (2), chlorhexidine salts represented by the formula (3) and pyridinium salts represented by the formula (4).

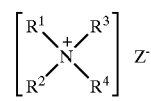

(1)

wherein, $R^1$ and $R^2$ are the same or different and represent long-chain alkyl, long-chain alkenyl or long-chain hydroxyalkyl groups each having 6 to 14 carbon atoms and totally having 16 to 26 atoms, $R^3$ and $R^4$ are the same or different and represent a $C_{1-3}$ alkyl group or hydroxyalkyl group or a polyoxyethylene group having an average addition mole of 10 or less, Z represents a halogen atom, an anionic residue of an amino acid, a fatty acid or a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may have a styrenesulfonic acid having a polymerization degree of 3 or greater or may have a hydrocarbon group as a substituent.

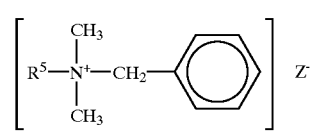

(2)

wherein, $R^5$ represents a $C_{8-14}$ hydrocarbon group or a group represented by the following formula:

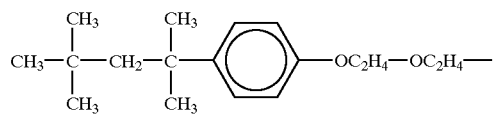

and Z has the same meaning as described above.

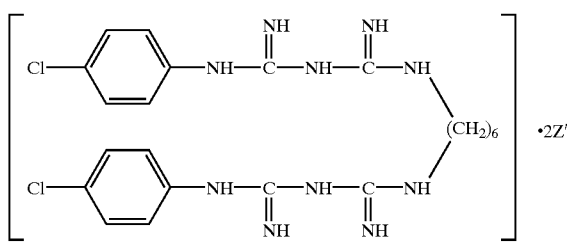
(3)

wherein, Z' represents gluconic acid, acetic acid or hydrochloric acid.

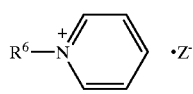
(4)

wherein, $R^6$ represents a linear or branched $C_{6-18}$ alkyl group and Z has the same meaning as described above.

In the formula (1), $C_{8-12}$ alkyl groups are preferred as each of $R^1$ and $R^2$, whereas $C_{1-3}$ alkyl groups are preferred as each of $R^3$ and $R^4$. In the formula (2), $C_{8-14}$ hydrocarbon groups are preferred as $R^5$. In the formula (4), $C_{8-16}$ alkyl groups are preferred as $R^6$.

In the formulas (1), (2) an (4), halogen atoms are particularly preferred as Z.

Specific preferred examples of the cationic surfactant include benzalkonium chloride, benzethonium chloride, cetylpyridinium chloride, chlorhexidine gluconate, chlorhexidine acetate and chlorhexidine hydrochloride, with those represented by the formula (2) such as benzalkonium chloride and benzethonium chloride being especially preferred.

As Component (B), use of an antibacterial cationic surfactant in combination with another antibacterial agent brings about higher effects. Component (B) is preferably incorporated in an amount of 0.005 to 5 wt. %, especially 0.1 to 4 wt. %, more preferably 0.4 to 3 wt. % in the whole composition. Within the above-described range, sufficient antibacterial effects are attained.

The glyceryl ether as Component (C) has a linear or branched $C_{4-12}$ alkyl or alkenyl group. Preferred are glyceryl ethers having a $C_{4-12}$ alkyl group such as n-butyl, isobutyl, tert-butyl, n-pentyl, isopentyl, n-hexyl, isohexyl, n-heptyl, n-octyl, 2-ethylhexyl, n-nonyl, n-decyl or n-lauryl. Of these, glyceryl ethers having a $C_{4-11}$ alkyl group, especially a $C_{6-10}$ alkyl group, more preferably a $C_8$ alkyl group are preferred, with the number of the alkyl groups being preferably 1 or 2, especially 1.

One or more of these glyceryl ethers can be used as Component (C). Incorporation of the glyceryl ether in an amount of 0.1 to 30 wt. %, especially 0.5 to 15 wt. %, more preferably 1 to 10 wt. % in the whole composition is preferred in order to impart the resulting detergent composition with excellent foaming performance.

In the detergent composition of the present invention, a metal chelating agent can be incorporated further to heighten its antibacterial effects. No particular limitation is imposed on the metal chelating agent insofar as it has a capacity of chelating metal ions. Examples include amono-polycarboxylic acid chelating agents, aromatic or aliphatic carboxylic acid chelating agents, amino acid chelating agents, ether polycarboxylic acid chelating agents, phosphonic acid chelating agents, hydroxycarboxylic acid chelating agents, phosphoric acid chelating agents, high-molecular electrolyte (including oligomer electrolyte) chelating agents and dimethyl glyoxime (DG). These chelating agents may be either in the form of a free acid or salt such as sodium salt, potassium salt or ammonium salt. Alternatively, they may be their hydrolyzable ester derivatives.

Specific examples of the amino-polycarboxylic acid chelating agents include:

a) compounds represented by the formula $R^{11}(Y)_2$,
b) compounds represented by the formula $N(Y)_3$,
c) compounds represented by the formula $R^{11}$—N(Y)—$CH_2CH_2$—$N(Y)_2$,
d) compounds represented by the formula $R_{11}$—N(Y)—$CH_2CH_2$—$N(Y)_2$,
e) compounds represented by the formula $(Y)_2N$—$R^{12}$—$N(Y)_2$, and
f) compounds analogous to Compound (e) and containing at least 4 Ys, for example, compounds represented by the following formula:

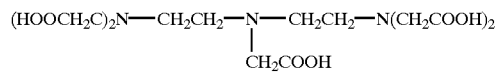

In the above formulas, Y represents —$CH_2COOH$ or —$CH_2CH_2COOH$, $R_{11}$ represents a group constituting a known chelating agent such as a hydrogen atom, an alkyl group, a hydroxy group or a hydroxyalkyl group, and $R^{12}$ represents a group constituting such a known chelating agent such as alkylene group or cycloalkylene group.

Typical examples of the amino-polycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH), and glycol ether diaminetetraacetic acid (GEDTA) and salts thereof.

Examples of the aromatic or aliphatic carboxylic acid chelating agents include oxalic acid, malonic acid, succinic acid, glutaric acid, adipic acid, itaconic acid, aconitic acid, pyruvic acid, salicylic acid, fumaric acid, acetylsalicylic acid, hydroxybenzoic acid, aminobenzoic acid (including anthranilic acid), phthalic acid, trimellitic acid and gallic acid, and salts, methyl esters or ethyl esters of these acids.

Examples of the amino acid chelating agent include glycine, serine, alanine, lysine, cystine, cysteine, ethionine, tyrosine and methionine, and salts or derivatives thereof.

Examples of the ether polycarboxylic acid chelating agents include diglycolic acid, compounds represented by the below-described formula, analogous compounds thereto and salts (e.g., sodium salt) thereof.

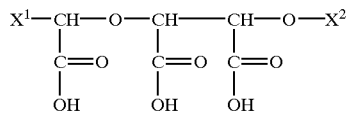

wherein, $X^1$ represents a hydrogen atom, —$CH_2COOH$ or —COOH, $X^2$ represents a hydrogen atom, —$CH_2COOH$ or

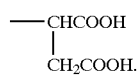

Examples of the phosphonic acid chelating agents include iminodimethylphosphonic acid (IDP), alkyldiphosphonic acids (ADPA) and 1-hydroxyethane-1,1-diphosphonic acid (DEQUESTT™ 2010).

Examples of the hydroxycarboxylic acid chelating agents include malic acid, citric acid, glycolic acid, gluconic acid, heptonic acid, tartaric acid and lactic acid, and salts thereof.

Examples of the phosphoric acid chelating agents include orthophosphoric acid, pyrophosphoric acid, triphosphoric acid and polyphosphoric acid.

Examples of the high-molecular electrolyte (including oligomer electrolyte) chelating agents include acrylic acid polymers, maleic anhydride polymers, α-hydroxyacrylic acid polymers, itaconic acid polymers, copolymers made of at least two of the monomers constituting these polymers, and epoxysuccinic acid polymers.

In addition, ascorbic acid, thioglycolic acid, phytic acid, glyoxylic acid and glyoxalic acid, and salts thereof can be preferably employed as a chelating agent.

Of these, preferred metal chelating agents include ethylenediaminetetraacetic acid (EDTA), succinic acid, salicylic acid, oxalic acid, lactic acid, fumaric acid, tartaric acid, and 1-hydroxyethane-1,1-diphosphonic acid, and salts thereof.

As the metal chelating agents, at least one of the above-exemplified ones can be used and it is preferably incorporated in an amount of 0.1 to 10 wt. %, especially 0.2 to 5 wt. % in the whole composition.

To the detergent composition of the present invention, components employed for ordinary detergent compositions may be added, for example, humectants such as propylene glycol, glycerin, diethylene glycol monoethyl ether, sorbitol and panthenol; conditioning components such as cationic polymers, silicone compounds and derivatives thereof; pearling agents such as ethylene glycol distearates; nonionic surfactants such as polyoxyethylene alkyl ethers and alkyl polyglucosides; amphoteric surfactants such as amidopropyl betaine; cationic components other than Component (B); coloring agents such as dye and pigment; viscosity regulators such as methyl cellulose, polyethylene glycol and ethanol; pH regulators such as citric acid and potassium hydroxide; and a salt such as sodium chloride, a vegetable extract, an antiseptic, a bactericide other than Component (B), a vitamin preparation, an anti-inflammatory agent, antidandruff, perfume, coloring matter, ultraviolet absorber, antioxidant and water, as needed.

The detergent composition of the present invention can be prepared in a manner known per se in the art and it is suited as hair or body detergents such as shampoo, body shampoo, face wash and hand wash.

EXAMPLES

Example 1

The detergent compositions having the formulations as shown in Table 1 were prepared in a manner known per se in the art and their detergency, quick foaming properties, antidandruff and deodorant effects were evaluated. The results are collectively shown in Table 1.

Evaluation Method (1) Detergency and Quick Foaming Properties:

A panel of male and female, each 5, healthy members shampooed their hair with each of the detergent compositions once a day for 1 week and evaluated its detergency and quick foaming properties based on the below-described criteria. An average score of 10 persons was found. The average scores of 4.0 or greater, 3.2 to 3.9, 2.5 to 3.1 and 2.4 or less were ranked "A", "B", "C" and "D", respectively.

5: Superior in feeling upon use

4: Slightly superior in feeling upon use

3: Normal in feeling upon use

2: Slightly inferior in feeling upon use

1: Inferior in feeling upon use (2) Antidandruff Effects

A panel of 5 male members shampooed their hair with each of the detergent compositions once a day for 1 month. After final shampooing, shampooing was terminated for about 48 hours, followed by shampooing twice, each with 3 g of the detergent composition. All the wash water after shampooing was collected and filtered through a 255 nylon mesh (100×100 μm) which had been weighed in advance. The weight of the horny cell layer trapped by the 255 nylon after air drying of the nylon mesh at room temperature for about 48 hours was designated as the weight of dandruff. An average weight of the dandruff of 5 persons was calculated and indicated by the below-described criteria.

A: weight of dandruff ≦ 30 mg.

B: 30 mg < weight of dandruff ≦ 40 mg.

C: 40 mg < weight of dandruff ≦ 50 mg.

D: 50 mg < weight of dandruff.

(3) Deodorant Effects

A using test of each of the detergent compositions by a panel of male and female, each 5, members was conducted once a day for 2 weeks. After final washing, the body odor of the panel members was evaluated by a trained panel of evaluators based on the below-described criteria. An average score of 10 persons was found. The average values of 4.0 or greater, 3.2 to 3.9, 2.5 to 3.1 and 2.4 or less were indicated by "A", "B", "C" and "D", respectively.

5: Odorless

4: With a slight odor

3: With an odor

2: With a noticeable odor

1: With a strong noticeable odor

TABLE 1

|  | Invention products | | | | Comparative product | | |
| --- | --- | --- | --- | --- | --- | --- | --- |
| Component (wt. %) | 1 | 2 | 3 | 4 | 1 | 2 | 3 |
| Sodium polyoxyethylene lauryl ether sulfate (EO = 2) | 15 |  | 15 | 10 | 15 | 15 | 15 |
| Sodium lauryl sulfate |  | 15 |  | 5 |  |  |  |
| n-Octyl glyceryl ether | 3 | 3 | 3 | 3 |  | 3 |  |

TABLE 1-continued

| Component (wt. %) | Invention products | | | | Comparative product | | |
|---|---|---|---|---|---|---|---|
| | 1 | 2 | 3 | 4 | 1 | 2 | 3 |
| Piroctone olamine | 1 | | 1 | | | | |
| Benzalkonium chloride ($C_{12}/C_{14}$ = 50/50) | | 0.5 | 0.2 | 0.5 | 0.5 | | |
| Disodium ethylenediaminetetraacetate | | | | 0.5 | | | |
| pH regulator/preservative/colorant/perfume | q.s. | q.s. | q.s. | q.s. | q.s. | q.s. | q.s. |
| Water | Balance | Balance | Balance | Balance | Balance | Balance | Balance |
| Detergency | A | A | A | A | C | B | C |
| Quick foaming properties | A | A | A | A | C | B | C |
| Antidandruff effects | A | A | A | A | C | D | D |
| Deodorant effects | A | A | A | A | C | D | D |

Example 2

The body shampoo having the below-described composition was prepared in a manner known per se in the art.

| (Component) | (wt. %) |
|---|---|
| Sodium polyoxyethylene cocoether sulfate (EO = 3) | 16 |
| n-Octyl glyceryl ether | 3 |
| Cetylpyridinium chloride | 1 |
| Disodium succinate | 1 |
| 1-Hydroxyethane-1,1-diphosphonic acid solution (60%) | 0.3 |
| Methylparaben | 0.2 |
| Cetanol | 0.5 |
| Perfume | 0.1 |
| Water | Balance |
| Total | 100.0 |

Example 3

The hair shampoo having the below-described composition. was prepared in a manner known per se in the art.

| (Component) | (wt. %) |
|---|---|
| Sodium polyoxyethylene lauryl ether sulfate (EO = 3) | 18 |
| n-Octyl glyceryl ether | 3 |
| Zinc pyrithione | 0.5 |
| Benzalkonium chloride ($C_{12}/C_{14}$ = 50/50) | 0.5 |
| Disodium succinate | 0.6 |
| Butylparaben | 0.2 |
| Perfume | 0.2 |
| Water | Balance |
| Total | 100.0 |

Example 4

The hand wash having the below-described composition was prepared in a manner known per se in the art.

| (Component) | (wt. %) |
|---|---|
| Ammonium polyoxyethylene lauryl ether sulfate (EO = 2) | 20 |
| n-Octyl glyceryl ether | 1 |
| Benzalkonium chloride ($C_{12}/C_{14}$ 50/50) | 1 |
| Disodium succinate | 0.8 |
| Disodium oxalate | 0.2 |
| Polyvinyl alcohol | 1 |
| Propylene glycol | 0.5 |
| Butylparaben | 0.2 |
| Pearling agent (ethylene glycol distearate) | 2 |
| Perfume | 0.3 |
| Water | Balance |
| Total | 100.0 |

Example 5

The shampoo as described below was prepared in a manner known per se in the art.

| (Component) | (wt. %) |
|---|---|
| Sodium polyoxyethylene lauryl ether sulfate (EO = 2) | 14 |
| 2-Ethylhexyl glyceryl ether | 2 |
| Zinc pyrithione | 0.8 |
| Benzalkonium chloride solution (50%) | 1.5 |
| Succinic acid | 0.3 |
| Sodium hydroxide | q.s. |
| Perfume | 0.3 |
| Water | Balance |
| Total | 100.0 |

The detergent compositions obtained in Examples 2 to 5 were each excellent in detergency and quick foaming properties and exhibited high antibacterial effects.

Industrial Applicability

The detergent compositions of the present invention have excellent detergency and quick foaming properties, exhibit high antibacterial action and bring about satisfactory antipruritic and deodorant effects on the scalp or body and antidandruff effects on the scalp.

What is claimed is:
1. A method of cleansing hair or skin comprising:
  washing hair, skin or hair and skin with a detergent composition comprising:
    (A) 5 to 50 wt. % of an anionic surfactant;

(B) 0.005 to 5 wt. % of an antibacterial agent; and
(C) 0.1 to 30 wt. % of a glyceryl ether having a $C_{4-12}$ alkyl or alkenyl group.

2. The method of claim 1, wherein Component (A) is selected from the group consisting of an alkyl sulfate, polyoxyalkylene alkyl ether sulfate or polyoxyalkylene alkenyl ether sulfate.

3. The method of claim 1, wherein Component (B) is an antibacterial agent selected from triclosan, triclocarban, piroctone olamine, zinc pyrithione, selenium disulfide and 3-methyl-4-(1-methylethyl)phenol.

4. The method of claim 1, wherein Component (B) is an antibacterial agent represented by any one of the following formulas (1) to (4):

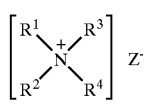
(1)

wherein, $R^1$ and $R^2$ are the same or different and represent long-chain alkyl, long-chain alkenyl or long-chain hydroxyalkyl groups each having 6 to 14 carbon atoms and totally having 16 to 26 atoms, $R^3$ and $R^4$ are the same or different and represent a $C_{1-3}$ alkyl group or hydroxyalkyl group or a polyoxyethylene group having an average addition mole of 10 or less, Z represents a halogen atom, an anionic residue of an amino acid, a fatty acid or a phosphate ester, phosphonate ester, sulfonate ester or sulfate ester having a linear or branched $C_{1-30}$ alkyl or alkenyl group, or an anionic oligomer or polymer containing a formalin condensate of a sulfonated polycyclic aromatic compound which may have a styrenesulfonic acid having a polymerization degree of 3 or greater or may have a hydrocarbon group as a substituent:

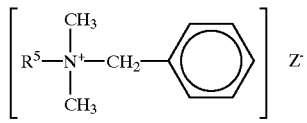
(2)

wherein, $R^5$ represents a $C_{8-14}$ hydrocarbon group or a group represented by the following formula:

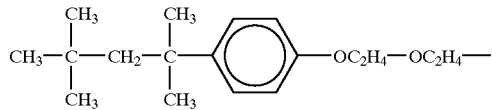

and Z has the same meaning as defined above:

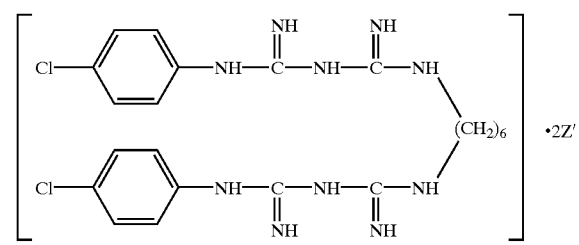
(3)

wherein, Z' represents gluconic acid, acetic acid or hydrochloric acid:

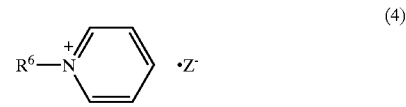
(4)

wherein, $R^6$ represents a linear or branched $C_{6-18}$ alkyl group and Z has the same meaning as defined above.

5. The method of claim 1, wherein said detergent composition further comprising a metal chelating agent.

6. The method of claim 1, wherein component (A) is present in an amount of 8 to 30 wt. %.

7. The method of claim 1, wherein component (A) is present in an amount of 10 to 22 wt. %.

8. The method of claim 1, wherein component (B) is selected from the group consisting of triclosan, triclocarban, piroctone olamine, zinc pyrithione and a mixture thereof.

9. The method of claim 1, wherein component (B) is present in an amount of 0.1 to 4 wt. %.

10. The method of claim 1, wherein component (B) is present in an amount of 0.4 to 3 wt. %.

11. The method of claim 1, wherein said glyceryl ether has a linear or branched $C_{4-12}$ alkyl or alkenyl group.

12. The method of claim 1, wherein the number of alkyl groups in said glyceryl ether is 1.

13. The method of claim 1, wherein the number of alkyl groups in said glyceryl ether is 2.

14. The method of claim 1, wherein component (C) is present in an amount of 0.5 to 15 wt. %.

15. The method of claim 1, wherein component (C) is present in an amount of 1 to 10 wt. %.

16. The method of claim 5, wherein said metal chelating agent is present in an amount of 0.1 to 10 wt. %.

17. The method of claim 5, wherein said metal chelating agent is present in an amount of 0.2 to 5 wt. %.

* * * * *